(12) United States Patent  (10) Patent No.: US 8,127,611 B2
Sharplin et al.  (45) Date of Patent: Mar. 6, 2012

(54) TIMBER HARVESTING APPARATUS

(75) Inventors: Nigel James Sharplin, North Canterbury (NZ); Peter Charles Stratton Carter, Papatoetoe (NZ)

(73) Assignee: Fibre-Gen Instruments Limited, Manukau, Auckland (NZ)

( * ) Notice: Subject to any disclaimer, the term of this patent is extended or adjusted under 35 U.S.C. 154(b) by 912 days.

(21) Appl. No.: 11/667,056

(22) PCT Filed: Nov. 3, 2005

(86) PCT No.: PCT/NZ2005/000292
§ 371 (c)(1),
(2), (4) Date: Apr. 7, 2008

(87) PCT Pub. No.: WO2006/049514
PCT Pub. Date: May 11, 2006

(65) Prior Publication Data
US 2008/0289724 A1    Nov. 27, 2008

(30) Foreign Application Priority Data
Nov. 4, 2004  (NZ) ...................................... 536400

(51) Int. Cl.
G01N 29/07  (2006.01)
G01N 33/46  (2006.01)
A01G 23/08  (2006.01)
G01H 5/00   (2006.01)

(52) U.S. Cl. .......................................... 73/597; 73/599
(58) Field of Classification Search .................. 73/597, 73/599
See application file for complete search history.

(56) References Cited

U.S. PATENT DOCUMENTS

| | | | |
|---|---|---|---|
| 5,097,881 A | 3/1992 | Mack | 144/356 |
| 6,347,551 B1 * | 2/2002 | Turpening et al. | 73/628 |
| 6,756,789 B1 | 6/2004 | Parker et al. | 324/637 |
| 2003/0093241 A1 | 5/2003 | Floyd et al. | 702/181 |
| 2005/0005699 A1 * | 1/2005 | Huang | 73/573 |
| 2005/0011263 A1 * | 1/2005 | Harris | 73/579 |
| 2005/0160819 A1 * | 7/2005 | Wang et al. | 73/632 |
| 2006/0000281 A1 * | 1/2006 | Harris | 73/579 |
| 2006/0185439 A1 * | 8/2006 | Harris | 73/760 |
| 2009/0188320 A1 * | 7/2009 | Greenough et al. | 73/602 |

FOREIGN PATENT DOCUMENTS
WO    WO99/44059    9/1999
* cited by examiner

*Primary Examiner* — Hezron E Williams
*Assistant Examiner* — Rose M Miller
(74) *Attorney, Agent, or Firm* — Jacobson Holman PLLC

(57) ABSTRACT

The use of a harvester head, processor head or merchandiser to deploy or place probes into a standing tree, felled stem or trunk, log, cant or the like whereby a time of flight of a stress or acoustic wave can be measured for the purpose of comparing a relationship to a threshold for the purpose of attributing a characteristic to be harvested, processed or broken down tree, stem or trunk, log, cant or the like.

40 Claims, 14 Drawing Sheets

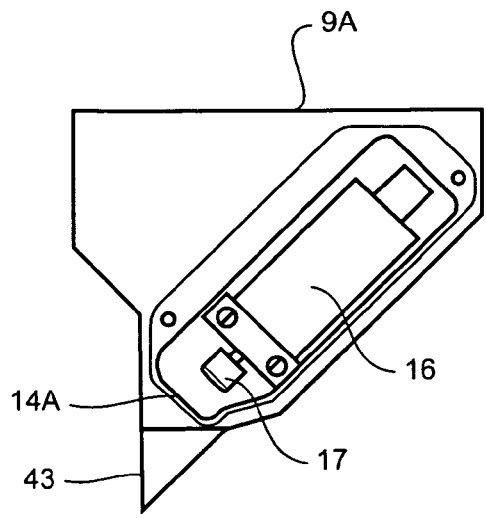
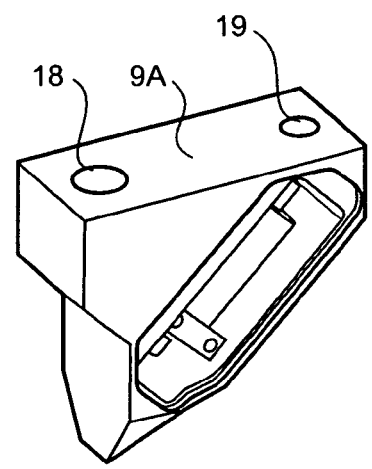
FIG. 9  FIG. 10
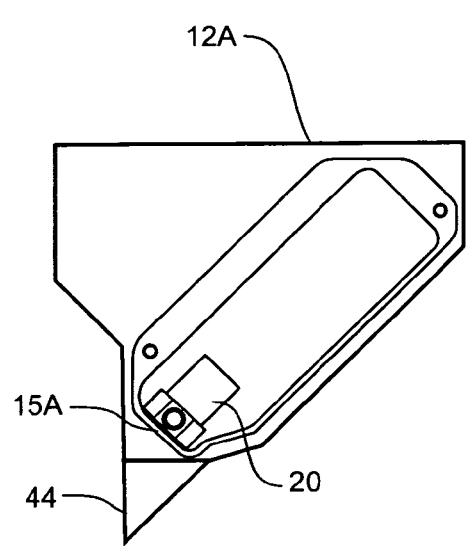
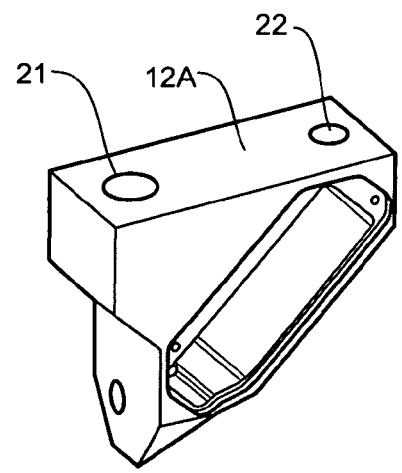
FIG. 11  FIG. 12

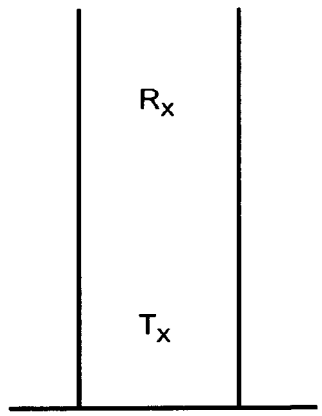 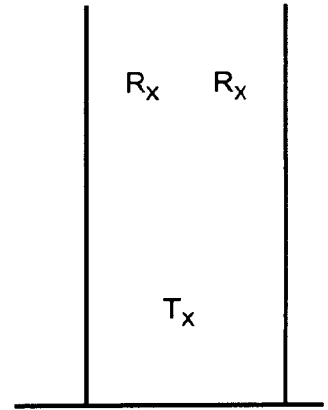
FIG. 23     FIG. 24
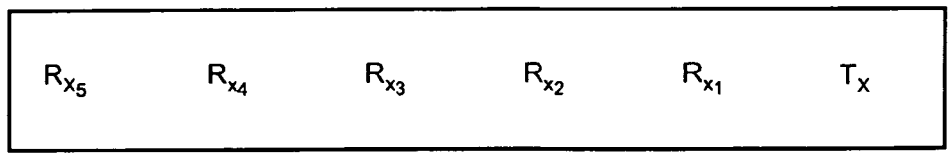
FIG. 25

TIMBER HARVESTING APPARATUS

This is a national stage of PCT/NZ05/000292 filed Nov. 3, 2005 and published in English.

A method of assessing a characteristic of a standing and/or recently felled tree and thereafter optionally taking such actions as are appropriate as a consequence of that assessment.

The timber industry faces a need to efficiently utilise its rather variable forest resources. This is true whether in New Zealand or elsewhere. Timber classification, for example, machine stress grading, is currently done at the end of the production chain although some earlier interventions have more recently been proposed. Stress grading, an example of late stage timber classification, results in wastage from processing which ultimately proves to be inappropriate. It is therefore more efficient to measure the log properties early in the chain and process the logs accordingly.

As used herein the term "logs" refers to logs cut from a tree or tree stem but can in certain circumstance also be applicable to the tree stem itself, cants cut therefrom, beams, boards, etc.

It is of course possible to assign different destinies to different logs to be cut from the same stem of a felled tree which will maximise the extracted value of harvesting of the particular tree. This has been recognised in New Zealand and elsewhere by software packages such as those of the New Zealand Forest Research Institute (i.e. the AVIS™ Software) or previously used by LIRO (i.e. the New Zealand Logging Industry Research Organisation).

In our New Zealand Patent Specifications 333434 and 337015, the full content of which is hereby included by way of reference, we disclose techniques useful early in the harvesting/processing chain reliant upon a FFT (Fast Fourier Transform) analysis of the wave pattern induced by reflecting sonic or the like stress waves in the tree-stem, logs, etc as a result of usually an impact induction of the sound or stress wave. Such apparatus and its methodology allows a reasonable estimation of modulus of elasticity (MOE) for a green felled log on the basis of an estimation of density of approximately 1000 kg/m$^2$ and thus at that early stage worthwhile decision making can be made.

Other systems contemplated also rely upon resolution of reflected sound waves. See, for example, New Zealand Patent Specification 506496 of Weyerhaeuser Company where breakdown decisions are to be made reliant upon reference to a price table that apparently takes heed of end product values and log characteristics that can be imputed to each of such logs from some average estimation for the felled tree stem.

Speed of transmission type testing as opposed to wave form resolution testing has been disclosed in U.S. Pat. No. 5,307,679 (Ross).

New Zealand Patent Specification 533153 (discloses hand held apparatus where two spiked probes are linked via an electronic unit with a timing device whereby stress waves imparted through one probe and its spike is timed in its passage to the second spiked probe thereby to enable the travel time of the stress wave from the first probe to the second probe to be determined for tree assessment purposes. Such apparatus is dependent upon manual positioning and manual activation to input the stress wave e.g. using an impact.

Other systems, rather than relying upon resolution of the fundamental frequency by FFT, instead rely upon analysis of a time elapsed process. One such example is that of Boardman, Graham and Tsehay all as disclosed in New Zealand Patent Specification 507297 the full content of which is here included by way of reference. That specification discloses the prospect of trees of lesser quality being identified early thus avoiding the milling of trees of inferior quality. NZ507297 in selecting trees for their assessed strength characteristics therein, is reliant on a time taken for the sound or stress wave to travel along the tree from its input point to a sensing spike. Such information is stated as being associable with a GPS location and data recording. There is also reference of manual marking by paint or the like.

The present invention envisages a useful advantage to be derived from an encounter between a harvester with its harvesting head and a still standing tree, the tree as it is being felled and/or a recently felled tree. In the case of a recently felled tree or tree stem, a merchandiser may alternatively be used to carry out the same or similar function. Reference herein therefore to the term "harvester" refers to a machine having a felling head and/or processing head and/or a merchandiser of any of the kinds contemplated in the aforementioned patent specification or as otherwise understood in the tree felling art as being a harvester or merchandiser. The term "processor" could in less preferred forms be a pruning head but in more preferred forms a harvester/processor combination.

The present invention also and/or alternatively recognises that a number of factors are relevant to an assessment of a standing tree at or immediately subsequent to its felling. Such factors include the species of tree, its estimated age, its girth as well as any estimation that might be made of its stiffness or other wood quality characteristics by reference to the speed of sound within the still green tree stem, whether standing or felled.

The present invention also and/or alternatively recognises that there is an advantage to be derived immediately prior to felling, during felling and/or immediately after felling to have characterised a particular part of the tree stem and immediately to mark the tree stem as to a characteristic, fate or the like dependent on the speed of sound or to immediately process in part the tree stem using a harvester head or merchandiser. The present invention sees an advantage in value extraction from a plantation of reliance upon remote operation from a vehicle of testing apparatus in conjunction with the harvester head and thereafter immediately using the harvester head responsive to the acoustic testing and/or remotely activating some marking procedure or instructing some marking procedure, or a combination of both.

Various forms of harvester are known.

See, for example, the pages 1 to 8 of Timber West Journal September/October 2002 that discusses harvesting and felling head heads specs of the following manufacturers: AFM-Forest Ltd, Caterpillar, Davco Manufacturing, Denharco, Fabtek, Gilbert Tech, Hahn Machinery, Hultdins, Keto/Hakmet, Loewen Forestry Equipment, LogMax, Pierce Pacific Manufacturing Inc, Ponsse, Quadco, Risley Equipment, Rotobec, Tigercat Industries Inc, Valmet/Timbco/Partek, Waratah Examples of such harvesting heads are disclosed in, for example, Valmet U.S. Pat. No. 4,537,236, Waratah U.S. Pat. No. 4,412,569, and Halm U.S. Pat. No. 4,382,457, amongst many others.

The present invention also as an option recognises an advantage in, at the harvester head or merchandiser (and preferably under the control of the operator of the harvester), having an appropriate inputting of data to the harvester operator or any recording or optimising apparatus or both of the outcome of any such testing and/or the harvester head marking of tree products derived from a standing tree prior to, at and/or immediately post felling and/or harvester head processing.

It is to one or more of these advantages that the present invention is directed.

U.S. Pat. Nos. 6,182,725 and 6,341,632 of Bengt Sorvik (both here included by way of reference) relates to a harvester being used in circumstances where data from pre-analysis of a forest region and location of individual trees in that region are tied to an accurate knowledge of the harvesting machine location of its harvesting head so as to appropriately harvest and/or harvesting machine process and mark tree parts immediately prior to felling, during felling or post felling. Such a system however is dependent on multiple inputs from diverse sources.

No mention is made to any tree, tree stem or log testing procedure by the harvester reliant on its own apparatus adapted, with or without harvester operator input, to provide an assessment. The present invention as an alternative or additional object recognises the value of a quality related decision in real time in a scientific and/or objective way at felling and subsequently.

As used herein the term "stress wave" envisages any sound, compression or other type wave that might be created by a suitable impact or sound input and which will run along and across the tree or tree stem, log or the like.

As used herein "elapsed time" relates to the time of passage or time of flight of a stress wave between sensors irrespective of whether or not one of those sensors is the input for the stress wave.

As used herein the term "and/or" means "and" or "or", or both.

As used herein the term "s" following a noun means the plural and/or singular forms of the noun.

As used herein the term "comprises" or "comprising" or any variation thereof consists only of and/or includes.

As used herein "grappling", or variants thereof, includes swing arm or other embracements.

As used herein "probe" or variations thereof includes preferably penetrative insertions of a transmitter and/or receiver surface.

In an aspect the invention is a harvester head or processor head of a kind adapted to grapple the trunk of a standing tree, the trunk of a felled tree or a log, the processor or harvester having a deployable grapple to hold the remainder of the head relative to a said trunk, a saw adapted to make a transverse cut where desired of trunk or log when the head has grappled the trunk or log, a drive to move the processor or harvester relatively along a said grappled trunk or log, a datum determining system to either treat or detect as a datum (i) the end being cut or to be cut as the tree is being felled, the end of trunk of the already felled tree or the end of the log, or (ii) the fresh end to be cut in the trunk of the already felled tree or in the log, a length determining system to measure the positioning of the saw for a processing cut from the datum determined by the datum determining system, first or second probes each deployable and capable of being withdrawn from deployment so that each penetrates a grappled trunk or grappled log at places longitudinally spaced on the trunk or log, the undeployed condition keeping the probes away from the trunk or tree to reduce exposure to damage when there is relativity of movement between the head and the trunk or log, and wherein there is a impact device or sound generator to provide a stress or sound wave input into the trunk when the probes are deployed in use, and wherein the time of flight of a longitudinally moving component of such stress or sound wave is determinable between the probes by involving wave sensing at the second probe and wave generation or wave sensing at the first probe, and wherein there is to be feedback to an operator or a control system, or both, as to the value of the time of flight, or a derivative thereof (e.g. velocity or a function thereof), or the relationship thereof to a threshold.

Preferably the head includes a debranching mechanism operative as said drive moves the processor or harvester along at least a grappled trunk.

Preferably the head carries a trunk or log cross sectional or diameter size determining system and there is to be feedback to an operator or a control system, or both, as to the relationship thereof to a threshold.

Preferably said first probe is a transmitter of the stress or sound wave and said second probe is a receiver of the stress or sound wave.

Preferably the transmission and receiving surfaces of the probes face towards each other at an acute angle to the longitudinal axis of the trunk or log. Preferably the acute angle is about 45°.

Optionally the probes are configured so as to reduce skewing upon deployment despite the acute angling.

Optionally the first probe is a transmitter by virtue of a switch actuated hammer or other impactor ("hammer") acting thereon or therein.

Preferably the switch provides a speed of light transmission to the second probe via cable or wireless means or the processor via cable or wireless means so that the stress or sound wave is known to be coming having been initiated at a time related to switch actuation.

In another aspect the invention is a processor head or harvester head of a kind able to grapple the trunk of a standing or felled tree, to transversely cut the trunk and, when not cutting transversely, of driving itself along a grappled trunk, wherein it carries at least two probes, (i.e. first and second probes) each deployable to penetrate at least the bark of a trunk that is grappled and is being held stationary relative to the head, and each capable of being withdrawn from the deployed condition, and wherein, whether through a probe or otherwise, a stress or sound wave generator of the head can cause a stress or sound wave to travel longitudinally of the trunk at least from or past a first probe to a second probe spaced longitudinally of the trunk, and wherein a processor determines an elapsed time of travel ("time of flight") of the wave between the probes.

Preferably the processor relates the time of flight, or a derivative thereof (e.g. velocity or a function thereof) to a threshold.

Preferably said first probe is a transmitter of the stress or sound wave and said second probe is a receiver of the stress or sound wave.

Preferably the transmission and receiving surfaces of the probes face towards each other at an acute angle to the longitudinal axis of the trunk or log. Preferably the acute angle is about 45°.

Optionally the probes are configured so as to reduce skewing upon deployment despite the acute angling.

Preferably the first probe is a transmitter by virtue of a switch actuated hammer or other impactor ("hammer") acting thereon or therein.

Optionally the switch provides a speed of light transmission via cable or wireless means to the second probe or via cable or wireless means to the processor so that the stress or sound wave is known to be coming having been initiated at a time related to switch actuation.

In another aspect the invention is a method of harvesting which comprises or includes grappling the trunk of a standing tree with a harvester head, deploying two probes from the head into the tree at positions spaced longitudinally on the trunk causing a stress or sound wave to travel longitudinally of the trunk from or past one probe ("first probe") to be received by the second probe ("second probe"), using processing means associated with inputs from at least one sensor or receiver, or both, associated with the second probe and at least one or more of a transmitter, sensor or switch associated with the first probe to obtain a time of flight of the stress or sound wave between the probes, and using the output of the processing means to cause automatically or with operator intervention at least one of
 (i) the head to fell the tree,
 (ii) the head to mark the tree,
 (iii) the head to fell the tree and to migrate on the felled tree to a distance from the felling cut and there to make a second cut,
 (iv) the head to fell the tree and to migrate on the felled tree to a distance from the felling cut and there to make a second cut and to mark or have marked the resultant log, Preferably, when the output is desirably to be structural timber or veneer, at least one or more of (i), (iii) and (iv).
 (a) follows or involves an operator or head determined relativity of the tree or trunk to a minimum stem/log cross sectional or diameter threshold for structural timber and
 (b) follows or involves, reliant on the output of the processing means, an operator or processing means determination that the time of flight or some value derived therefrom is suitable for milling as structural timber.

In another aspect the invention is a processor head or harvester head of a kind able to grapple the trunk of felled tree or a log, wherein it carries at least two probes, (i.e. first and second probes) each deployable to penetrate at least the bark of a trunk or log that is grappled and is being held stationary relative to the head, and each capable of being withdrawn from the deployed condition, and wherein, whether through a probe or otherwise, a stress or sound wave generator of the head can cause a stress or sound wave to travel longitudinally of the trunk or log at least from or past a first probe to a second probe spaced longitudinally of the trunk, and wherein a processor determines an elapsed time of travel ("time of flight") of the wave between the probes.

Preferably the processor relates the time of flight, or a derivative thereof (e.g. velocity or a function thereof) to a threshold.

Preferably said first probe is a transmitter of the stress or sound wave and said second probe is a receiver of the stress or sound wave.

Preferably the transmission and receiving surfaces of the probes face towards each other at an acute angle to the longitudinal axis of the trunk or log. Preferably the acute angle is about 45°.

Optionally the probes are configured so as to reduce skewing upon deployment despite the acute angling.

Preferably the first probe is a transmitter by virtue of a switch actuated hammer or other impactor ("hammer") acting thereon or therein.

Preferably the switch provides a speed of light transmission via cable or wireless means to the second probe or via cable or wireless means the processor so that the stress or sound wave is known to be coming having been initiated at a time related to switch actuation.

In still another aspect the invention is a method of processing which comprises or includes grappling the trunk of a felled tree or a log with a harvester or processor head, deploying two probes from the head into the trunk or log at positions spaced longitudinally of the trunk or log, causing a stress of sound wave to travel longitudinally of the trunk or log from or past one probe ("first probe") to be received by the second probe ("second probe"), using processing means associated with inputs from at least one sensor or receiver, or both, associated with the second probe and at least one or more of a transmitter, sensor or switch associated with the first probe to obtain a time of flight of the stress or sound wave between the probes, and using the output of the processing means to cause automatically or with operator intervention at least one of
 (a) the head to mark the trunk or log,
 (b) the head to migrate relative to but on the trunk or log to a distance from the felling cut or a fresh cut and there to make a second cut,
 (c) the head to migrate relative to but on the trunk or log to a distance from the felling cut or a fresh cut and there to make a second cut and to mark or have marked the resultant log,
 (d) the head to migrate relative to but on the trunk or log to a distance from the felling cut or a fresh cut and there to make a second cut and to debranch or have debranched the resultant log,
 (e) the head to migrate relative to but on the trunk or log to a distance from the felling cut or a fresh cut and there to make a second cut and to mark or have marked the resultant log and to debranch or have debranched the resultant log.

Preferably, when the output is desirably to be structural timber or veneer, at least one or more of (a), (b), (c), (d) and (e)
 (a) follows or involves an operator or head determined relativity of the trunk or log to a minimum stem/log cross sectional or diameter threshold for structural timber and
 (b) follows or involves, reliant on the output of the processing means, an operator or processing means determination that the time of flight or some value derived therefrom is suitable for milling as structural timber.

In another aspect the invention is a method of in forest segregating, classifying or grading of standing trees, felled trees, or logs thereof, or any of the foregoing, which method involves a grappling harvester head or processor head having penetrative probes and using the probes to relate a time of flight of a stress or sound wave between the probes to one or more threshold for streaming purposes.

In another aspect the invention is the use of a trunk or log grappling harvester head or processor head to deploy probes literally into, and to un-deploy the probes from, the trunk or log (i) to allow, by their use, when deployed, a time of flight of a sound wave or stress wave between them along the trunk or log to be sensed and (ii) to allow when undeployed, the head to drive itself along the trunk or log, or vice versa.

In another aspect the invention is a method of assessing trees which comprises or includes engaging a head of a vehicular harvester or processor to a felled or unfelled tree or engaging a merchandiser to a felled tree or part thereof, (prior to, during and/or post felling) sensing between probes carried by the head or merchandiser the elapsed time of one or more stress waves within the tree (or tree stem or part thereof) induced from and/or by apparatus carried by the head, and assessing the status of that tree (or tree stem or part thereof) on the basis of or, on the basis of some derivative of, the elapsed time.

In an aspect, the present invention relates to a method of assessing trees which comprises or includes engaging a harvester or merchandiser head to a tree, (prior to, during and/or post felling) sensing between sensors or probes carried by the head the elapsed time of one or more stress waves within the tree (or tree stem or part thereof) induced from and/or by apparatus carried by the head, and assessing the status of that tree (or tree stem or part thereof) on the basis of, or the basis of some derivative of, the elapsed time.

Preferably there are is one transmitting probe and two equidistant receiving probes and the shorter time or times of that one receiving probe is preferred to the other's.

In another aspect the invention is a method of harvesting trees using a harvester head, which method comprises or includes positioning the harvester head with respect to the tree (preferably engaging the harvester head to the tree)

causing or allowing harvester head carried apparatus to measure an elapsed time for a stress wave, to travel from one sensor to another, the stress wave having been induced by apparatus carried by the head, and making decisions as to the harvesting and/or non harvesting of that tree (optionally and preferably reliant on the harvester head) in response to such measure.

In another aspect the invention is a method of harvesting trees using a harvester head, which method comprises or includes positioning the harvester head with respect to the tree (preferably engaging the harvester head to the tree)

causing or allowing harvester head carried apparatus to measure an elapsed time for a stress wave to travel from one sensor to another, the stress wave having been induced by apparatus carried by the head, and marking that tree in response to such measure reliant upon marking apparatus (optionally carried by the harvester head).

In another aspect the invention is a method of assessing trees using a harvester head, which method comprises or includes positioning the harvester head with respect to the tree (preferably engaging the harvester head to the tree), causing or allowing harvester head carried apparatus to sense a stress wave travelling from or past one sensor to another in the tree (prior to, during and/or post felling), each carried by the harvester head, the stress wave optionally having been created or induced by apparatus also carried by the head, and assessing at least part of the tree as to a characteristic reliant on the elapsed time of travel between the sensors.

Preferably the method involves supplying the elapsed time or derived velocity to the operator or an optimiser such that log making or product decisions relating to recovery of improved value can be made, accounting for velocity and the characteristic.

The present invention also consists in any processing and/or harvesting system (or apparatus and/or methods) which involves any of the steps or series of steps embodied in FIGS. 1 and/or 2 and/or 3 of the accompanying drawings or which uses apparatus substantially as depicted in any one of FIGS. 4 to 6 or is otherwise substantially as herein described.

In still a further aspect the present invention consists in a harvesting machine, the harvester head of a harvesting machine, or a harvesting head suitable for incorporation in a harvesting machine where the harvesting head directly or indirectly carries sensors adapted when against and/or in the tree or tree stem or logs thereof (e.g. if already felled) to sense a stress wave travelling in the tree, tree stem or log, the apparatus including means (i) to initiate the stress wave travel so that it will travel from one, or past first one, and then to and/or past the second of the sensors.

(ii) to determine an elapsed time of travel between the sensors, and/or (iii) to generate a decision signal for the fate of the tree/tree stem/log to the harvester operator and/or some responsive tree/tree-stem/log marking or log making device.

In still a further aspect the present invention consists in the use in a standing tree or a felled tree trunk or log of a transmitter probe and two equidistant receiver probes deployed from and/or carried by a harvester head to derive a time of flight value, or derivative thereof, as a result of one or more stress or sound impulses from the transmitter probe, the value or its derivative being for that component of the wave or waves that travels quicker (i.e. lower elapsed time) such as to better estimate time of flight independent of branch stubs, knots or other factors which may reduce the measured time of flight.

Preferably the value, or derivative thereof, is compared to a threshold or threshold values for a decision making purpose.

Preferably the use is coupled to a harvester determined minimum girth or diameter of the tree, trunk or log.

Preferably the decision making purpose involves marking or a cut or cuts to be made by the harvester head.

In still a further aspect the present invention consists in the use of spaced probes on a merchandiser to provide a sequence or overlap of time of flight values, or derivatives thereof, to provide a profile longitudinally of a log, cant or the like to be broken down on the merchandiser.

In another aspect the invention is the assessed and/or harvested and/or processed product of such apparatus and/or methodology.

The present invention envisages preferably some time between the harvester head clamping the tree (loosely or tightly) and the harvester head indexing along the tree, the data set being collected. A data set can preferably be collected by repetitive inputs during a data collection so as to provide a mean velocity output notwithstanding the fact that preferably the sensors for each such input are not moved. The present invention also envisages the prospect of more than two sensors particularly where there is a desire to provide the impact input via a sensor, and where there is a likelihood that one or more of the sensors will happen to be located upon a knot or branch stub. In such situation elapsed time and velocity measures from the sensor contacting the branch stub or knot would be lower than a typical measure for the stem or log and would be ignored in subsequent derivation of fate or marking.

In another aspect the invention is, at a breakdown merchandiser, a method to determine breakdown involving longitudinally spacing probes into an elongate feedstock stem, log, cant or the like, inducing a stress or sound wave longitudinally of the stem, log, cant or the like, deriving time of flight information of the induce wave between adjacent probes, and breaking down the stem, log, cant or the like reliant on the times of flight derived.

Preferred forms of the present invention will now be described with reference to the accompanying drawings in which FIG. 1 shows a first scenario where a harvester approaches a standing tree, the flow diagram showing a variety of steps that can be utilised in order to provide a desired assessment etc and downstream steps, FIG. 2 in a similar manner to that of FIG. 1 shows a flow diagram for a felled tree/tree stem/log at a harvest site or skid site again showing downstream procedures, FIG. 3 is a third scenario showing a stem/log quality test system involving a merchandiser system, FIG. 4 shows a vehicle with a boom carrying a processor head i.e. the whole vehicle and processor head might be considered as a harvester irrespective of whether or not the processor or harvester head is clamped to a standing tree or dangles and is clamped to an already felled tree, there being shown a tree in proximity, FIG. 5 shows the processor head of the harvester of FIG. 4 embracing a tree, FIG. 6 shows aspects of a processor head insofar as the data transmission between receive probe and processor (data transmission being shown by the broken lines) is concerned, FIG. 7 is a plot showing with use of apparatus in accordance with the present invention the batch average log velocity (expressed in km/second) against the proportion of stems of a plantation that might have been selected, plot showing that if, for example, 100% of the trees are felled and selected the average log velocity is below 3.05 km/second whereas if only say 50% of the trees are selected for cutting reliant on apparatus of the present invention an average log velocity of at least 3.1 is achievable thus meaning that such felled logs are over a threshold that might lend themselves to cutting to length suitable for structural timber and for milling to structural timber, the present invention being independent of where an appropriate threshold is for decision making between output destined for structural timber and output not destined for structural timber (e.g. industrial timber e.g. apple boxes, pulping, etc.), FIG. 8 shows a pair of probes having a transmitter labelled Tx and a receiver labelled Rx capable of being inserted into the wood surface shown so as to impart from the transmitter Tx a sound or stress wave with a longitudinal component capable of being detected as a longitudinal component by the receiver Rx, the Tx and Rx surfaces being parallel and normal to the trunk or log longitudinal axis, FIG. 9 is a side elevational view in a diagrammatic form showing one form of transmitter Tx with a solenoid capable of driving the Tx hammer, the Tx hammer preferably having a hammer and switch encounter, FIG. 10 is a perspective view of the arrangement as shown in FIG. 9 showing how the chamber housing the solenoid and Tx hammer can be closed, FIG. 11 is a similar view to that of FIG. 9 but showing an accelerometer in the chamber, the Rx accelerometer being shown against a vibration receiving face, FIG. 12 is a similar view to that of FIG. 10 but showing the probe for the Rx accelerometer, FIG. 13 shows an alternative form of probe less liable to deflection when being advanced into the bark of a tree under the action of a hydraulic ram (not shown) so as to allow the solenoid driven hammer shown to act thereon, FIG. 14 is a perspective view of the transmitter probe of the FIG. 13, FIG. 15 is a similar view to that of FIG. 13 but of a receiver or accelerometer including probe to compliment the transmitter probe of FIGS. 13 and 14, FIG. 16 is a perspective view from the ram end of the probe, FIG. 17 is another perspective view of the probe of FIGS. 15 and 16, FIG. 18 shows proof of concept proving apparatus in conjunction with a log, tree stem section or standing tree section showing two linked jig assemblies each adapted to be chain clamped (chain not shown) to the log or the like (thereby to simulate grappling) and to allow a hydraulic ram in each case to press the probe transversely of the longitudinal axis of the log or the like so as to provide penetration preferably through the bark and preferably slightly into the wood to provide a better transmission and receiving encounter with the log or the like, FIG. 19 is a plot of the detected sound or stress wave (multiple impact inputs) so that the time can be determined along the X axis from the time of the impact to the detection of the first part of the first received sound wave, such subsequent periodic impacts allowing, if desired, a greater degree of accuracy as a result of verification, averaging or the like, FIG. 20 is a perspective view of part of a WARATAH™ type processor/harvester (the assembly showing the saw and some other components not in place), the drawings showing a preferred position for a ram (e.g. hydraulic) deployable and a ram (e.g. solenoid) actuable transmitter probe (e.g. Tx) and at least one ram (hydraulic) actuated receiving probe (e.g. Rx), which probes are not deployed until the processor/harvester is bound tightly (e.g. by grappling arms) to the tree, tree trunk, log or the like and is un-deployed prior to any loosening of the grip on the test item thereby to avoid damage to the probes and the support structure, FIG. 21 is another view of the apparatus of FIG. 20, FIG. 22 is a diagram of the relationships involved in using apparatus as in FIG. 18, FIG. 23 shows a standing tree with two probes only (Tx and Rx), FIG. 24 is similar to FIG. 23 but with two Rx each equidistant from Tx, and FIG. 25 is similar to FIG. 23 but with multiple Rx probes at fixed distances along the log, cant or the like.

The present invention envisages in a plantation situation a processor/harvester enabled to approach still standing trees, be clamped thereto (e.g. by grappling pivoted arms hydraulically actuable) in which the time of flight of an impact caused sound or stress wave is utilised against a threshold to determine a characteristic of the tree and one or more of the following occurs:

the information is stored in respect of that tree
the tree is marked according to the determination
the tree is felled responsive to that determination
the tree is felled in accordance with that determination and the processor/harvester measures a length L from the cut of the harvester to enable the processor/harvester to make a subsequent cut.

Optionally the processor/harvester debranches the logs being formed or the trunk.

It is envisaged with any one of the foregoing options the processor/harvester can mark the still standing tree or felled tree or cut log.

In the case of an already felled tree or previously partly processed log it is envisaged that the processor can attach to the felled tree trunk and go to an end as the datum, or provide a fresh trim of an end as a datum, thereby to enable assessment of a time of flight and thereafter a determination of a characteristic to be followed by marking
movement to make a cut to log length
debranching if required.

In a merchandiser situation it is envisaged that multiple probes spaced by known distances would be transversely inserted into a preferably stationary or longitudinally advancing log, cant or other elongate wood item thereby to allow along the length thereof a plurality of assessments of time of flight thereby to enable cut decisions transversely of the elongate axis to be made.

Preferred forms of the present invention will now be described with reference to FIG. 1 where a harvester approaches a standing tree. (The contents of that flow diagram are here included by way of reference).

FIG. 2 similarly shows a flow diagram for a felled tree or tree stem or log (and again the contents of that flow diagram are here included by way of reference).

The present invention envisage the mounting of the device in conjunction with a log/tree processor head or merchandiser (variously referred to as a harvester head, processor, processor head, harvesting attachment, single grip harvester, stroke delimiter, feller buncher, merchandiser or similar).

One option uses two sensor probes such that a stress wave preferably initiated to the third probe inserted between or preferably outside of the two receive probes so that an elapsed time for such a stress wave were it to move directly between the receive probes can be determined. Preferably the initiation probe preferably outside of the others is inserted with orientation or an angle such that a longitudinal stress wave can be automatically initiated by an actuator. Such an actuator to be struck or triggered is preferably capable of being struck or triggered several times in rapid succession (e.g. by using a hydraulic percussion, electric solenoid or similar device) thereby to enable as many as ten or more waves to be created and captured by the receive probes and analysed. Initiation and measurement time must be rapid to minimise possible impact on harvesting or merchandiser productivity.

Preferably each receive probe will incorporate a (preferably piezo electric) accelerometer designed that they can be inserted as hydraulically driven spikes or other mechanically driveable means through the bark and into the outer wood of the tree/stem/log to a depth of preferably from 1 to 2 cm past the cambium and into the wood. Most ideally the receive probes will be at or around one metre apart although there could be a greater distance (possibly two to three metres) or more depending on the harvester or merchandiser equipment to which it is attached.

The shape of the probes is preferably such that insertion will be possible at right angle to the surface of the tree/stem/log but the embedded accelerometer orientation such that they are capable of detecting the longitudinal stress wave as it passes. The probes and supporting mechanicals are preferably sufficiently robust or protected to withstand normal wear and tear in a typical harvester head or merchandiser working environment. Preferably perceived signals will be analysed using an approach as disclosed in any of the aforesaid specifications or in Australian Patent Application No. 2005200236 mentioned hereinafter i.e. by identifying the true wave arrival time and the elapsed time between the probes determined by subtractive or such other analysis as may be appropriate dependent on the initiator probe placement.

Such an approach preferably minimises the interference caused by other sound travelling through the stem/log from the equipment.

Preferably the analysis is performed using electronic processing means (computer, micro-processor) located preferably near the received probes and the output of such analysis will be transferred by cable or wireless connection to the machine operator's cab. Output will preferably be in the form of the velocity of sound which can be compared against user defined thresholds for input into optimiser software to support decision making on log products to be manufactured from the tree/stem/log. Paint or other marking device carried by the harvester apparatus may then be actuated in response to determined velocity relative to thresholds to mark tree/stem/log according to velocity determined grade.

FIG. 3, the full content of which is here included by way of reference, shows a merchandiser system in accordance with the present invention.

FIG. 5 shows the articulatable arm 5 at two limits of its preferred movement with respect to a specific tree stem, such articulation being operable under the action of a hydraulic ram.

Figure 1:
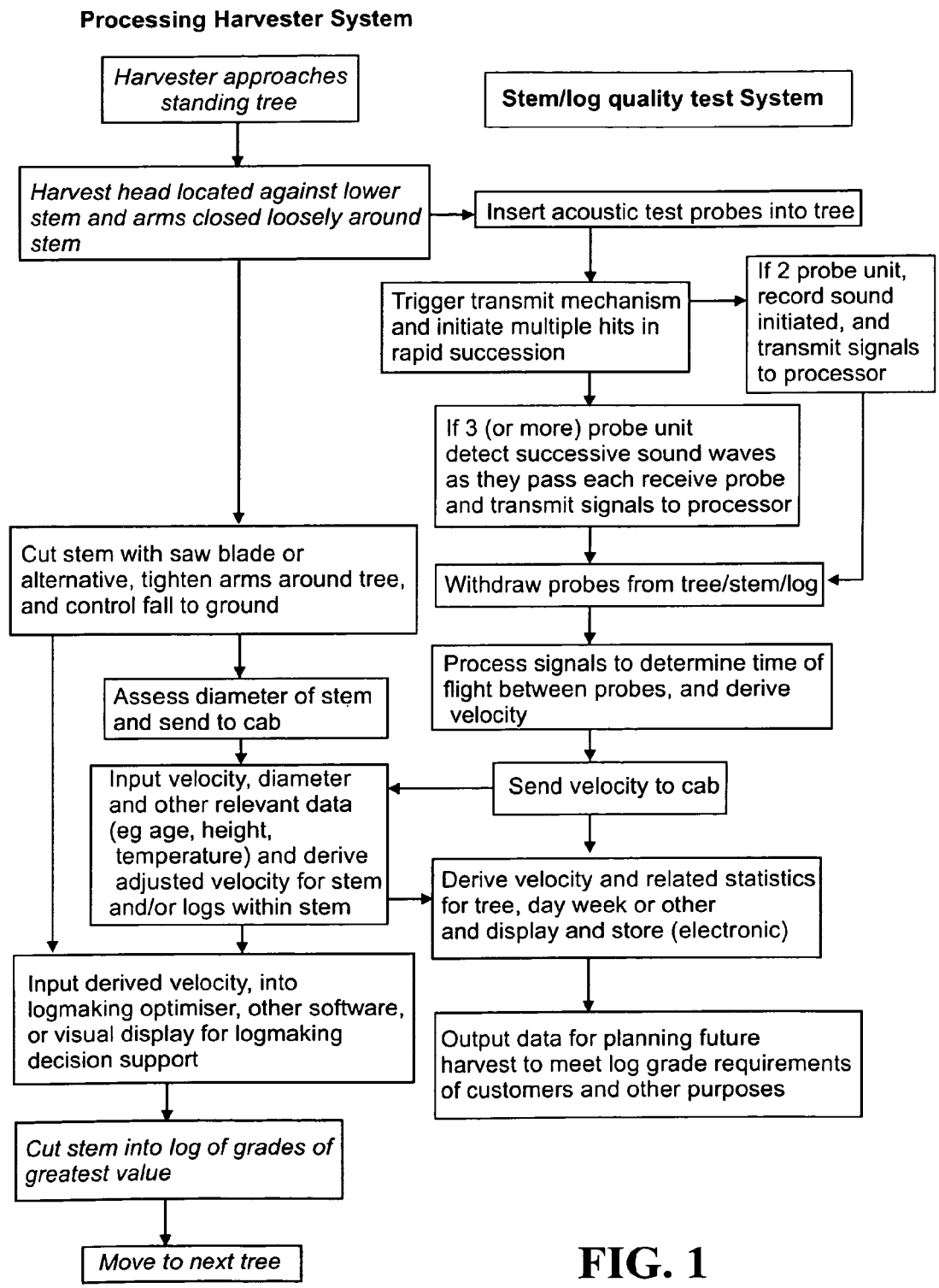
Figure 2:
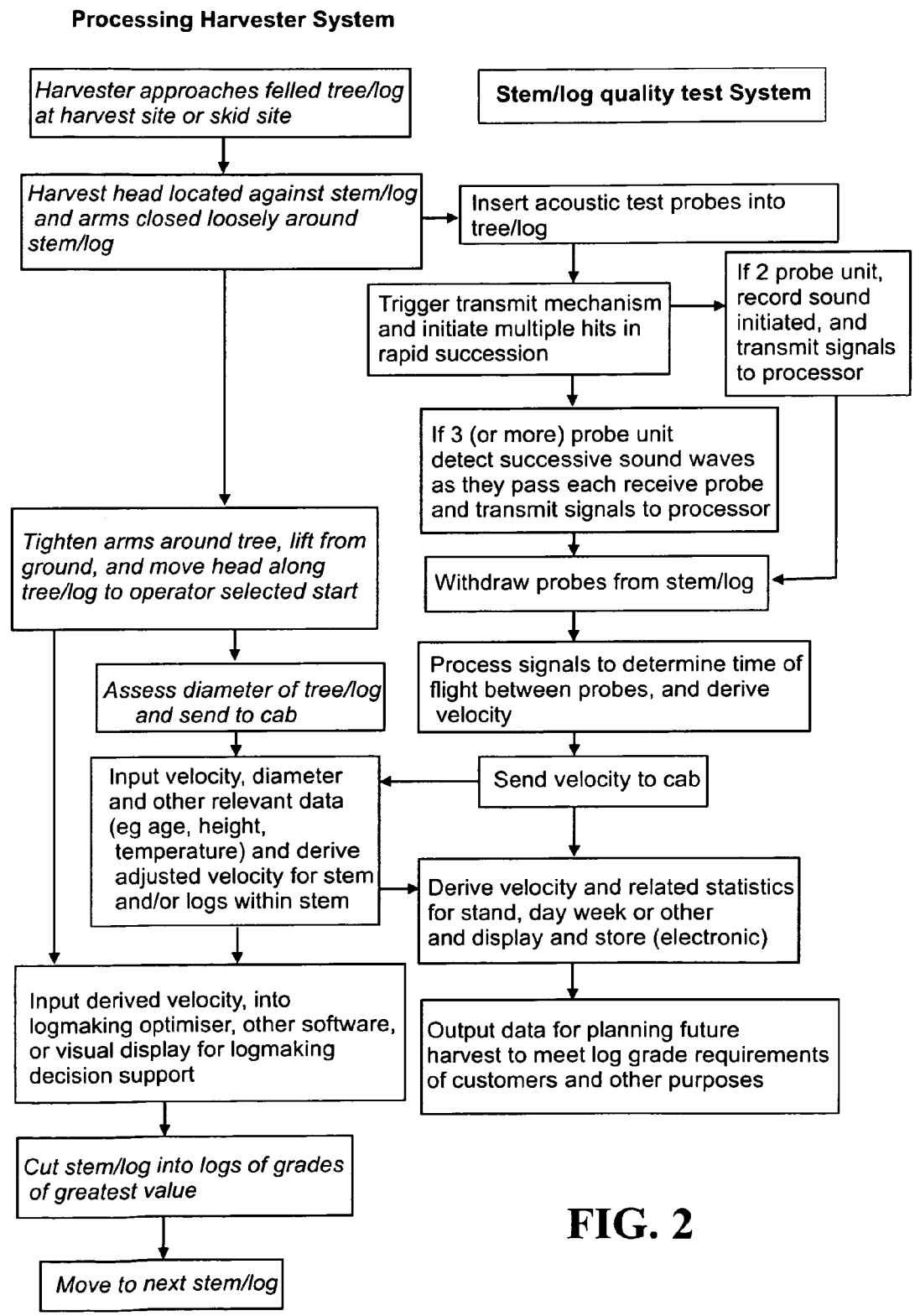
Figure 3:
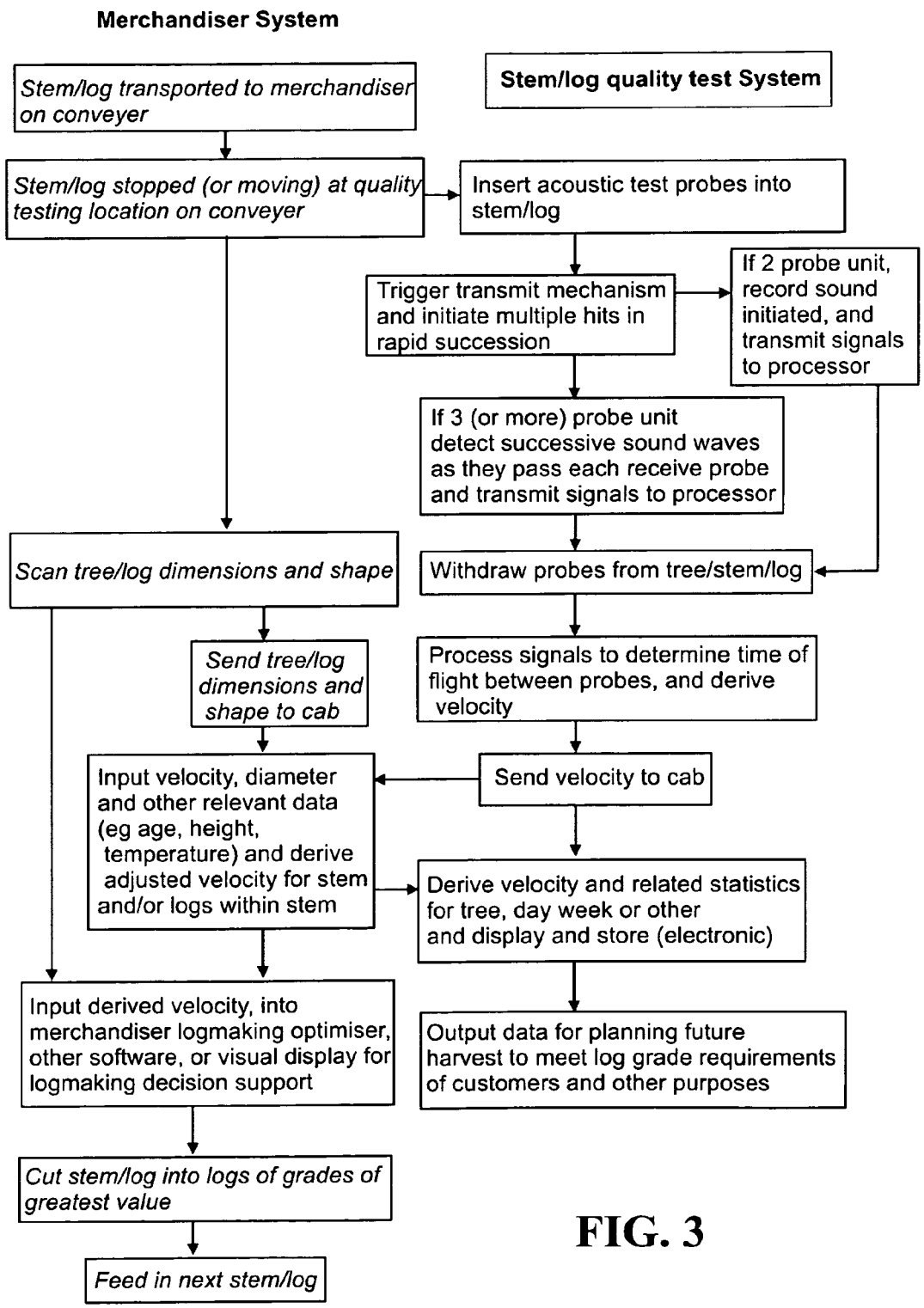
Figure 4:
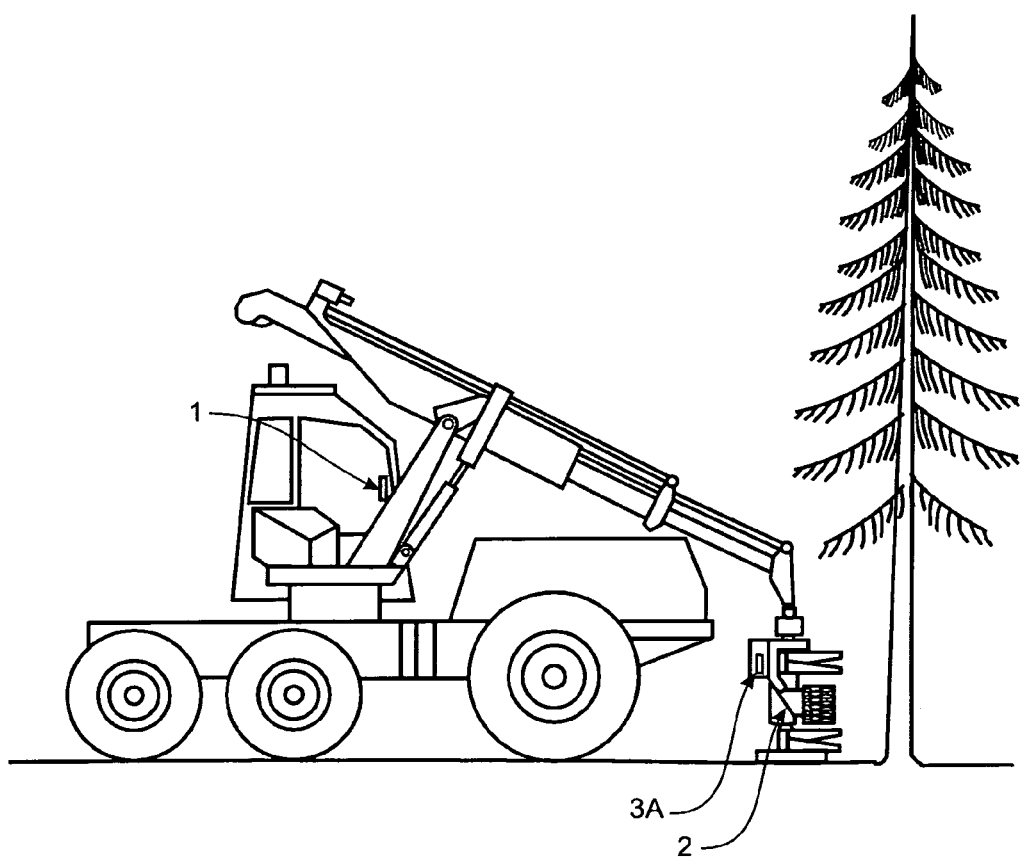
FIGS. 4 through 6 show preferred apparatus in accordance with the present invention there being depicted as 1 the operator/user interface preferably to which data is transmitted from a signal processor 3A and 3B, such data being from probes 4A and 4B respectively.
Figure 6:
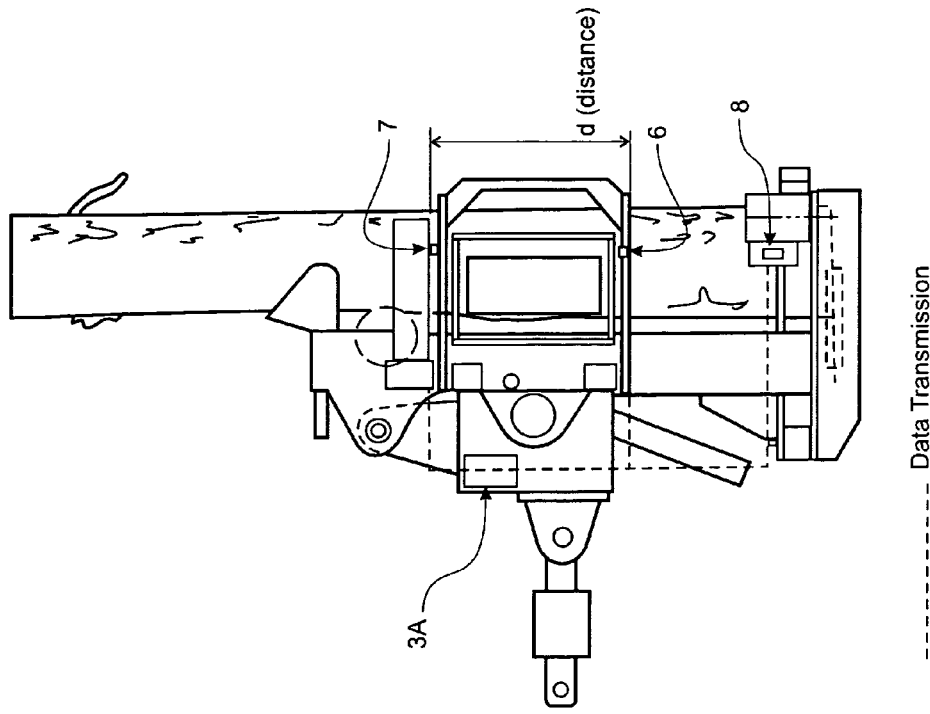
Figure 5:
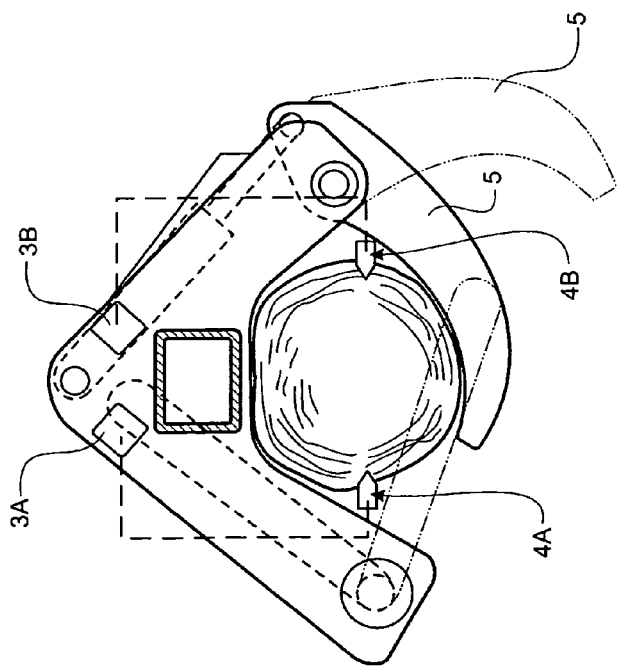

FIG. 6 shows spaced a distance D apart receive probes 6 and 7 respectively whilst that probe 8 is preferably the transmit probe capable of being user interface operated or operated in conjunction with the clamping of the tree. Preferably the probes (at least the receive probes) penetrate the wood to a depth of at least 1 to 2 cm. The probes are preferably forced in under the clamping action but not necessarily so i.e. they could be independently driven by remotely actionable means (e.g. solenoids, rams, etc.) controllable at the user interface.

The testing apparatus includes two probes as a minimum, preferably each to penetrate the wood of the test item preferably by a depth of at least 1 to 2 cm. Preferably the spikes angle towards each other.

It discloses as at its publication date a first and second acoustic probe, each in the form of a spike, able to be driven through the bark and cambium into the sapwood, if desired, attachable to a tree at different heights to engage the wood of the trunk and to provide an acoustic transmission signal and an acoustic reception signal indicating, respectively, a time of initiation of an acoustic wave into the wood by the first acoustic probe and a time of receipt of the acoustic wave through the wood at the second probe. The probes are adapted to transmit a longitudinal compression wave through the bulk wood (both sapwood and heartwood) in the tree from the first probe to the second probe and to detect longitudinal compression wave passing through the tree at the second probe. Analysis circuitry communicating with the first and second acoustic probes may receive an acoustic transmission signal (start signal) and an acoustic reception signal (stop signal) to provide a speed of sound measurement of the acoustic wave through the wood. A wireless communication link may transmit at least one of the acoustic stop signal and acoustic start signal to the analysis circuitry, the wireless communication link providing a speed of transmission substantially greater than a speed of propagation of the acoustic wave.

The wireless communication link may be infrared diode transmitting the acoustic start signal from the first probe to the analysis circuitry.

Figure 7:
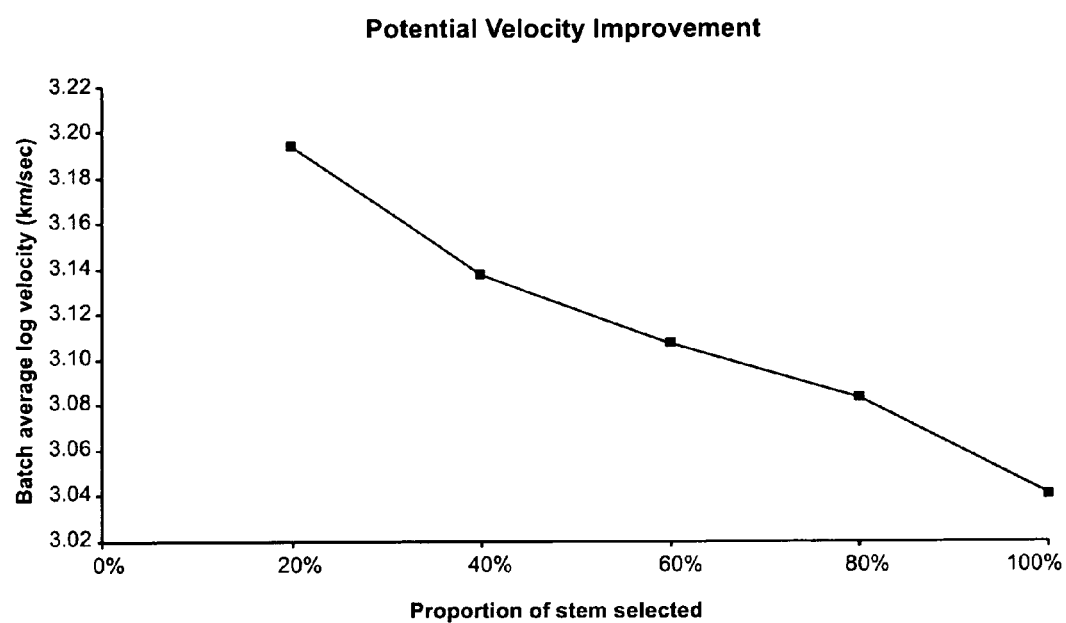

FIG. 7 shows a plot of batch average log velocity (km/second) against proportion of stem selected showing how with apparatus in accordance with the present invention it is possible by being selective of the trees in a plantation of assessing the average velocity detected from a standing tree or a recently felled tree thereby to improve assessment as suitable or less than suitable for breakdown as, for example, structural lumber. Obviously other outputs by way of decision making can be made from such velocity information inclusive of suitability for pulping, suitability for use in engineered wood products, fibre length, microfibril angle etc.

Preferred forms of the present invention however will describe in more detail by reference to probes and supporting systems suitable for use with a harvester/processor preferably of a kind typified by that of Waratah Forestry Attachments of Tokoroa, New Zealand (see their website at www.waratah.net) and particularly their WARATAH™ HTH200, HTH400 and HTH600 series harvester heads/processor heads.

Figure 8:
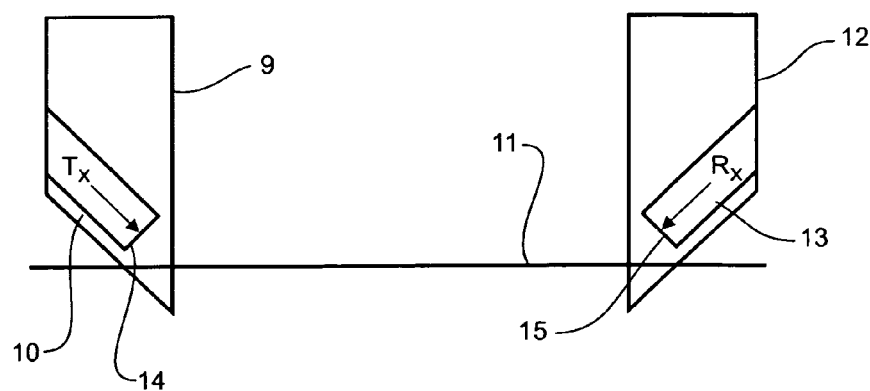
Figure 15:
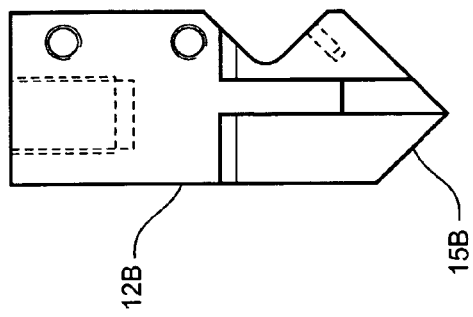

FIG. 8 shows two probes 9 (as a transmitter probe Tx) and a receiver probe 12 (as a receiver probe Rx) but where each can penetrate into a wood surface 12 by, for example, 25 mm, yet still have an initial transmission face 14 of Tx and a receiving face 15 of receiver Rx at an angle to the longitudinal axis of the tree trunk or log having the wood surface 11. Notwithstanding the inclination of the surfaces 14 and 15 however it can be seen that with the asymmetric forms of each probe there is a transmission surface facing towards a receiving surface of the other probe which is substantially normal to the wood surface 11.

The same is the situation with a transmitter probe 9A shown in FIG. 9 where the probe has a surface 14A corresponding with that of 14 to be hit by a hammer 17 under the action of a solenoid 16. As can be seen in FIG. 10 the arrangement depicted has a ram mount 18 and a cable access at 19.

Similarly the receiver probe 12A has an inclined receiver surface 15A for an accelerometer 20. Notwithstanding the angling of the surface to be hammered (14A) and the accelerometer face 15A that can be seen, the final faces 43 and 44 will be mutually parallel and normal to the longitudinal axis of the log.

The receiver probe 12A has a ram mount 21 (e.g. for a hydraulic ram) as well as a cable axis way 22.

Figure 14:
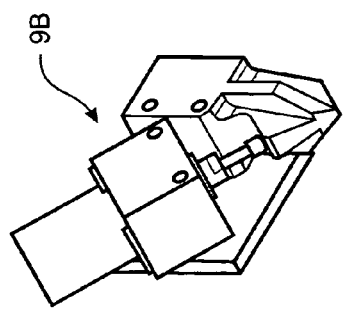
Figure 13:
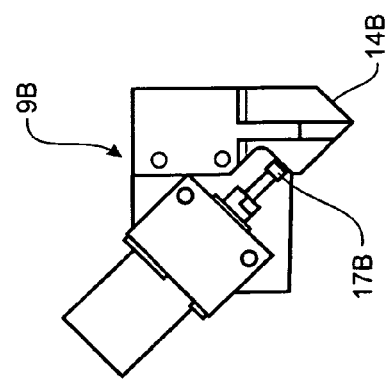
Figure 17:
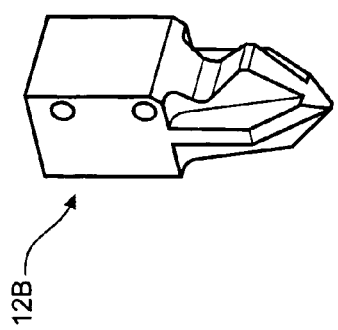
Figure 16:
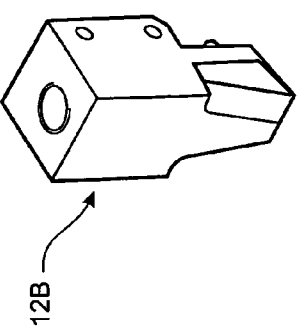

More preferred is a transmission probe such as shown in FIGS. 13 and 14 where the probe assembly 9B has a solenoid actuated hammer 17B that impacts on a probe adapted to minimise skewing on lateral penetration of a trunk or log yet which presents an acute angle face 14B as the transmission surface.

Similarly the receiver probe 12B again with an anti-skewing configuration, has an angled receiving face 15B for the accelerometer which complements the transmission surface acute angle 14B. Such acute angles are preferably about 45° but can be between 20° and 90° relative to the stem/tree/log surface. Such angling of Tx and Rx towards each other leads to better amplitudes being detected.

Figure 18:
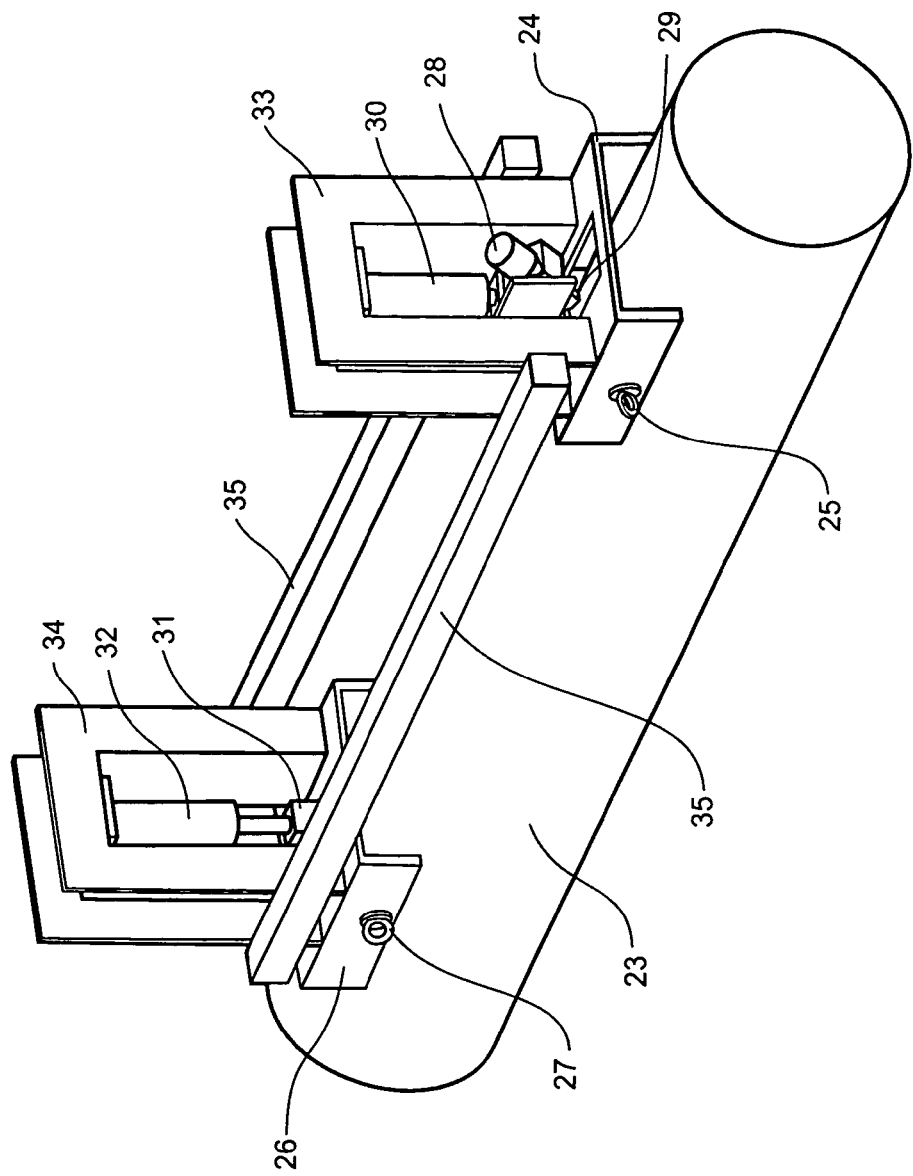

FIG. 18 shows a rig utilised to demonstrate the viability of the system of the present invention. Shown is a log or tree trunk simulation 23 on which sits a pair of saddles 24 and 26 to be held there by encircling chains (not shown) attached to coupling points 25 and 27 respectively. These chains simulate the grappling arms contemplated for a harvester such as a Waratah harvester of the series previously referred to.

Shown supported by the saddle 24 is a support structure 33 from which a hydraulic ram 30 is mounted to drive the probe 29 penetratively into the log 23. Carried with that probe is the hammering solenoid 28.

Spaced by members 35 from the frame support 33 is a frame support 34 from which a hydraulic ram for the receiver probe 31 depends.

Figure 20:
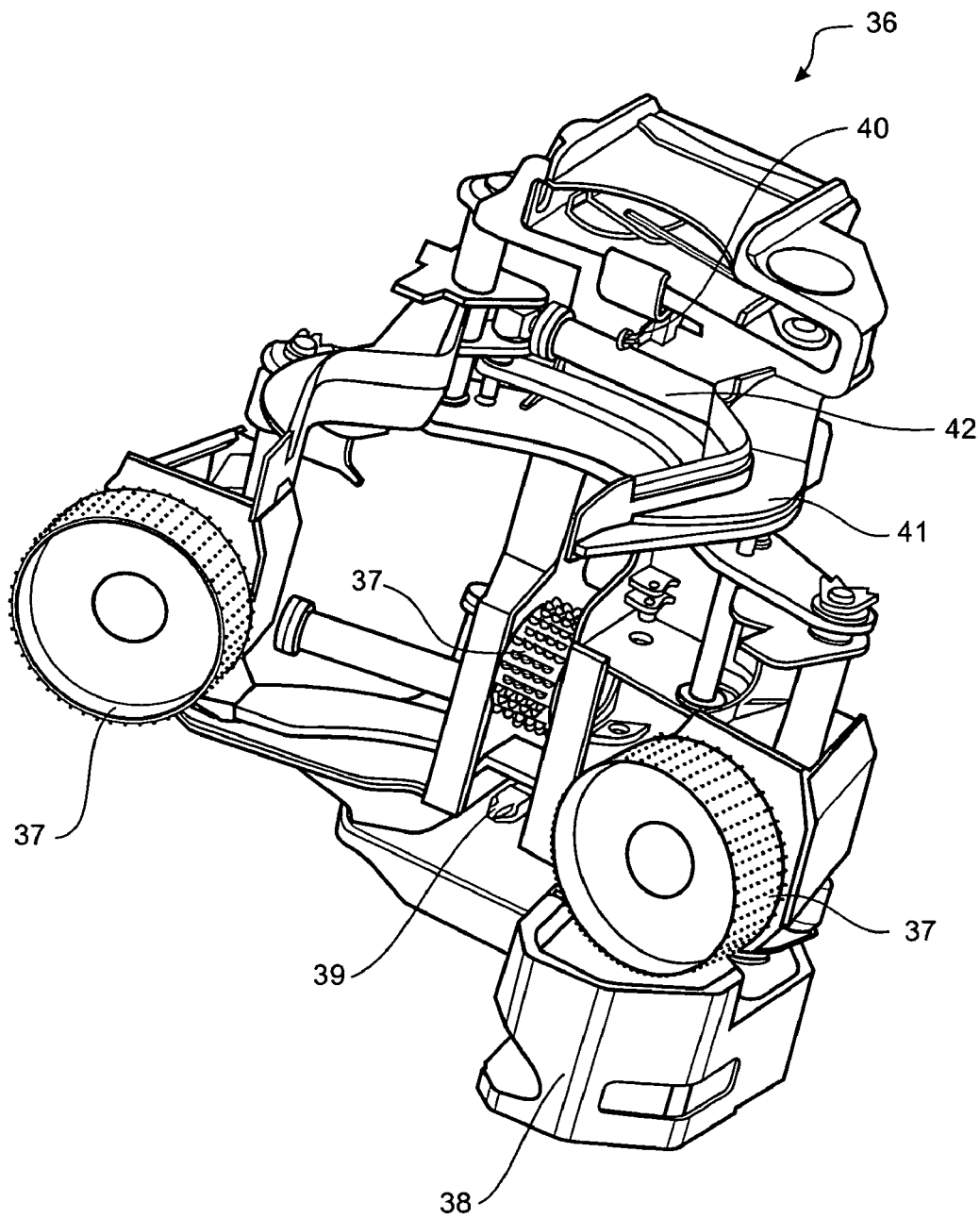
Figure 21:
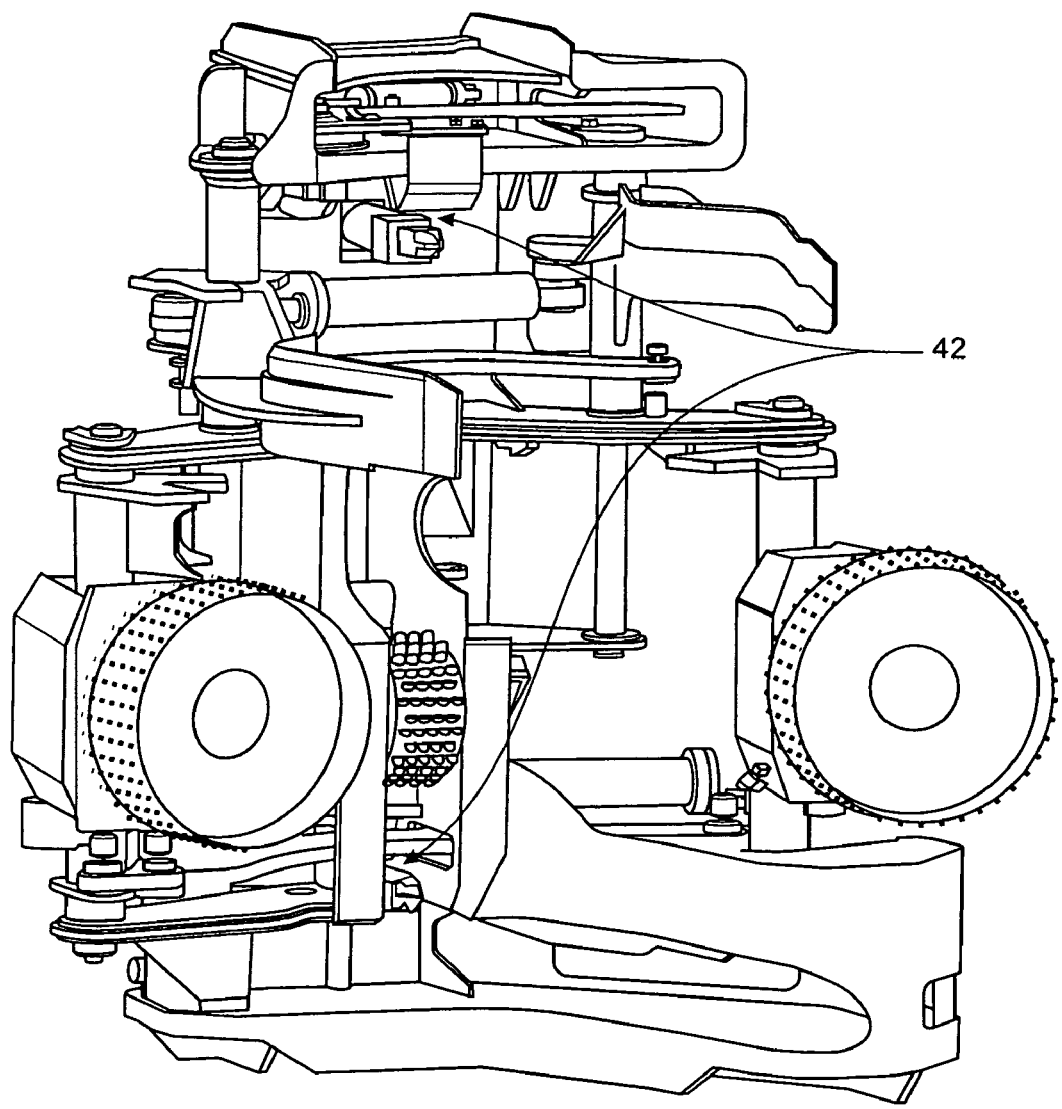

Such a rig simulates the arrangement contemplated where there is a transmitter probe Tx to be hydraulically driven (e.g. from a lower part of a harvester head) and one or preferably a pair of equally distant receiver probes (e.g. mounted more upwardly) in the harvester head. FIG. 20 shows in part together with FIG. 21 a Waratah HTH600 series harvester but without a number of components shown including the pruning devices (for delimbing) and without the transverse cutting saw. There is at least one and preferably several grappling arms 41 actuable to embrace a standing tree or a felled tree or log under the actions of a hydraulic ram 42. Also shown are drive wheels 37 adapted (e.g. under the action of hydraulic motors) to allow the vehicle supported harvester head or processing head to move a tree trunk or log through the harvester for the purpose of allowing delimbing and also for the purpose of moving the head from its felling cut position (as a datum) to a second cut position that is preferably determined by reference to the acoustic characteristic of the standing or felled trunk or log. Such distance traveled from the datum is to be known as it occurs by the control system or operator, or both, using appropriate inputs.

Shown are a single transmitter probe 39 and a single receiver probe 40.

Figure 19:
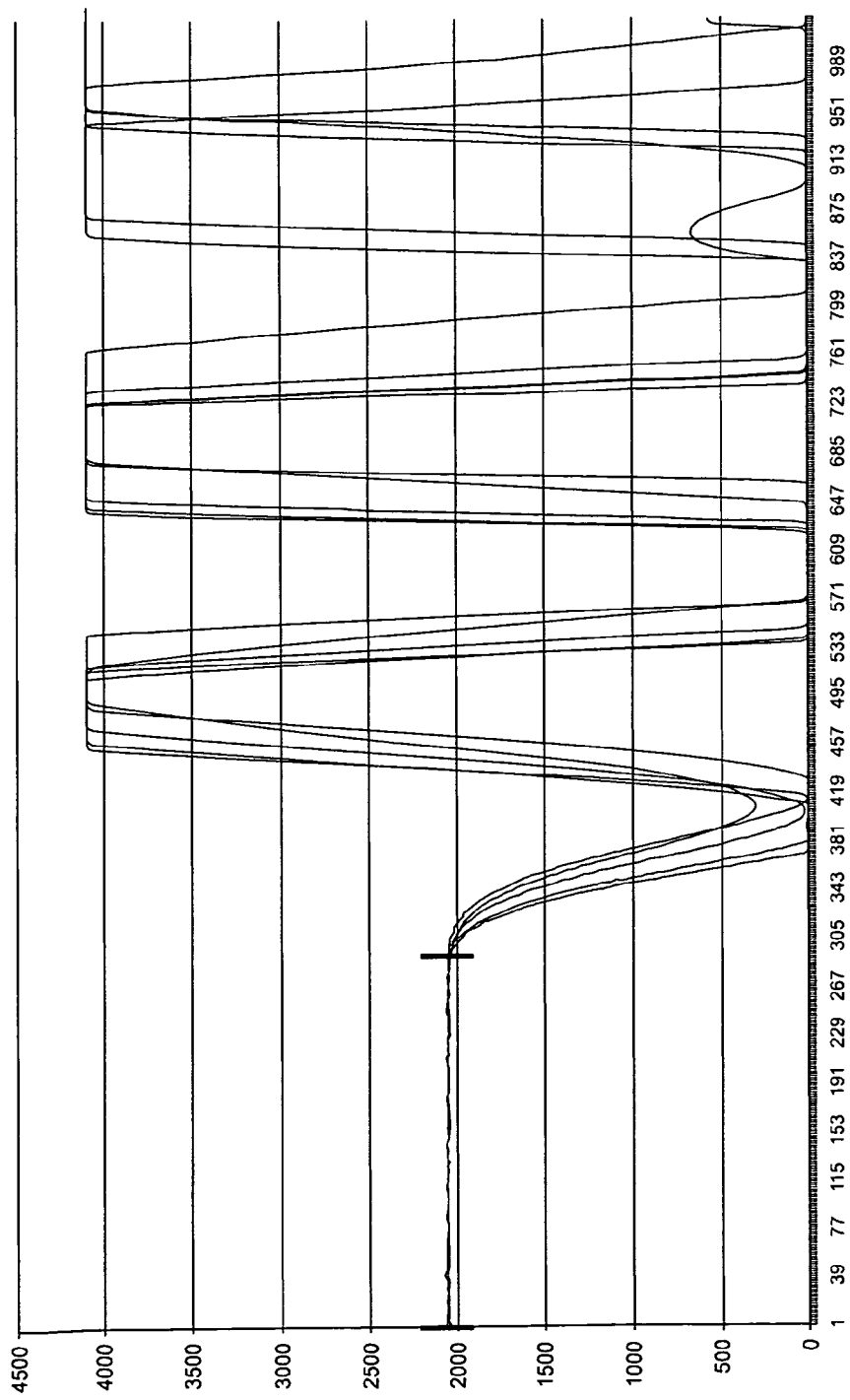

As will be described with reference to FIG. 22 with respect to the apparatus where the viability of the system was tested, one or more strikes provides a sequence of wave forms as shown in FIG. 19 with the elapsed time, and thus the "time of flight", being derived between the vertical lines marked on the plot for ease of explanation.

Figure 22:
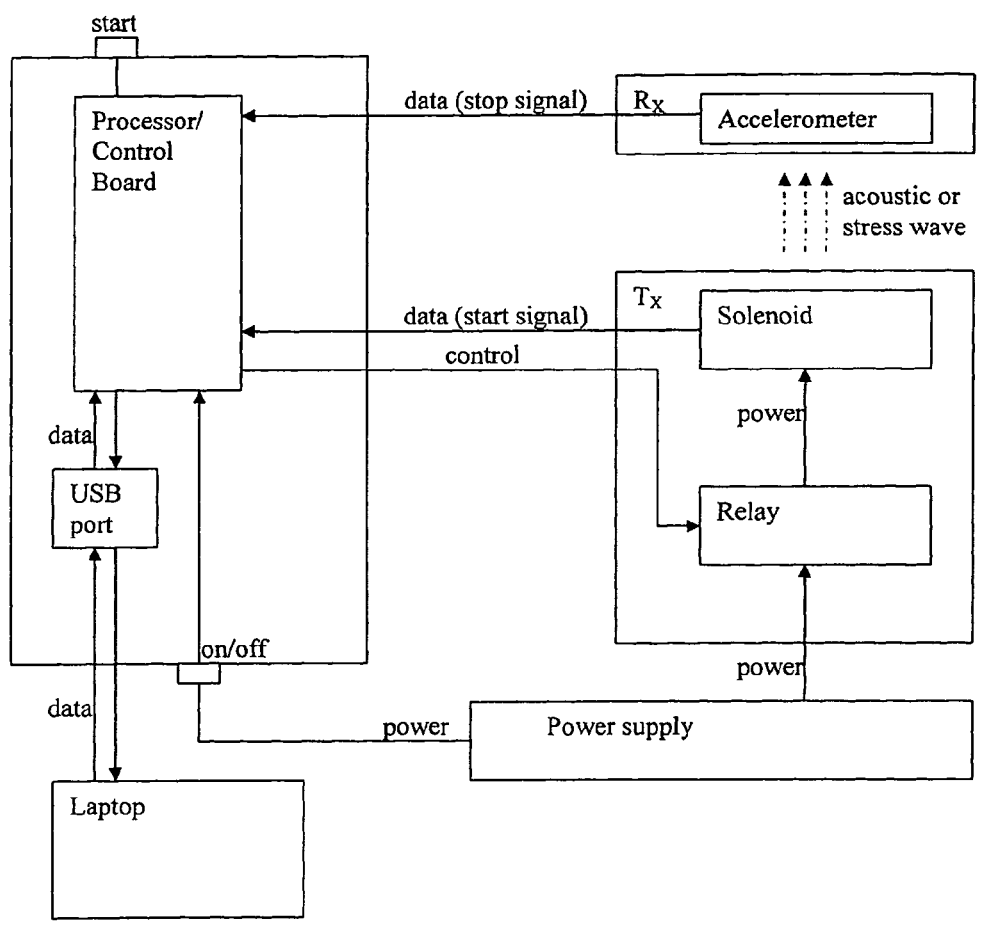

FIG. 22 shows a flow diagram used in conjunction with the test wood of FIG. 18 where the Rx receiver probe with its accelerometer is linked via a processing board (for example an ST300 board) as is the Tx transmitter probe. Shown are relays, solenoid, controls and the like to and from the board as well as a switching mechanism for powering up the board. Also shown is a USB connected laptop through the board which can be used for processing and data storage purposes.

In the preferred form of the present invention rather than the arrangement shown in FIG. 23 where there is a lower transmission point Tx aligned with an upper receiving point Rx, preferably equally distanced penetrative probes Rx are provided (as in FIG. 24) from the transmission probe Tx thereby allowing the shortest elapsed time to be taken as representative of the longitudinal component of the stress or sound wave. This allows a discounting of any knot interference with one of the Rx probes. The lower Tx probe should be less likely to encounter knots. It is envisaged that several impacts from the transmission hammer (for example 3) in less than half a second will provide good accuracy over a distance between the transmission probe and the receiving probes of, for example, 1500 mm.

In a merchandiser application of the present invention as depicted in FIG. 25 multiple Rx probes are located at fixed distances along the stem/log/cant or the like, enabling time of flight or derivatives thereof to be determined at various points along the stem/log/cant.

The invention claimed is:

1. A harvester head or processor head adapted to grapple a trunk of a standing tree, a trunk of a felled tree or a log, comprising
    a deployable grapple to hold the remainder of the head relative to the trunk or log,
    a saw adapted to make a transverse cut in a desired location in the trunk or log when the head has grappled the trunk or log,
    a drive to move the processor or harvester relatively along the grappled trunk or log,
    a datum determining system to either treat or detect as a datum (i) the end being cut or to be cut as the tree is being felled, the end of trunk of the already felled tree or the end of the log, or (ii) the fresh end to be cut in the trunk of the already felled tree or in the log, a length determining system to measure the positioning of the saw for a processing cut from the datum determined by the datum determining system, first and second probes each deployable and capable of being withdrawn from deployment so that each penetrates the grappled trunk or grappled log at places longitudinally spaced on the trunk or log, the undeployed condition keeping the probes away from the trunk or tree to reduce exposure to damage when there is relativity of movement between the head and the trunk or log, an impact device or sound generator to provide a stress or sound wave input into the trunk when the probes are deployed in use, an electronic processor determining the time of flight of a longitudinally moving component of the stress or sound wave between the probes by involving wave sensing at the second probe and wave generation or wave sensing at the first probe, the electronic processor providing feedback to an operator or a control system, or both, as to the value of the time of flight, or a derivative thereof, or the relationship thereof to a threshold.

2. The head of claim 1 wherein the head includes a delimbing mechanism.

3. The head of claim 1 wherein the head carries a trunk or log cross sectional or diameter size determining system and there is to be feedback to an operator or a control system, or both, as to the relationship thereof to a threshold.

4. The head of claim 1 wherein the first probe is a transmitter of the stress or sound wave and the second probe is a receiver of the stress or sound wave.

5. The head of claim 4 wherein the transmission and receiving surfaces of the probes face towards each other at an acute angle to the longitudinal axis of the trunk or log.

6. The head of claim 5 wherein the acute angle is about 45°.

7. The head of claim 5 wherein the probes are configured so as to reduce skewing upon deployment despite the acute angling.

8. The head of claim 1 wherein the first probe is a transmitter by virtue of a switch actuated hammer or other impactor acting thereon.

9. The head of claim 8 wherein the switch provides a transmission via cable or wireless means to the second probe or via cable or wireless means to the processor so that the stress or sound wave is known to be coming having been initiated at a time related to switch actuation.

10. The use of a trunk or log grappling harvester head or processor head of claim 1 to deploy probes laterally into, and to un-deploy the probes from, the trunk or log
(i) to allow, by their use, when deployed, a time of flight of a sound wave or stress wave between the probes along the trunk or log to be sensed and
(ii) to allow when undeployed, the head to drive itself along the trunk or log, or vice versa.

11. The method of assessing trees, said method comprising engaging a harvester head or processor head of claim 1 of a vehicular harvester or processor to a felled or unfelled tree or engaging a merchandiser to a felled tree or part thereof,
sensing between probes carried by the head the elapsed time of one or more stress waves within the tree induced from and/or by apparatus carried by the head, and
assessing the status of the tree on the basis of or, on the basis of some derivative of, the elapsed time.

12. The method of harvesting trees using a harvester head of claim 1, said method comprising positioning the harvester head with respect to the tree,
causing or allowing a harvester head carried apparatus to measure an elapsed time for a stress wave, to travel from one probe to another, the stress wave having been induced by the apparatus carried by the head, and
making decisions as to the harvesting of the tree in response to the measure.

13. The method of claim 12 wherein the positioning involves the grapple engaging the harvester to the tree.

14. The method of claim 12 wherein each decision to harvest involves, or is followed by, use of the harvester to fell each tree.

15. The method of harvesting trees using a harvester head of claim 1, said method comprising
positioning the harvester head with respect to the tree,
causing or allowing a harvester head carried apparatus to measure an elapsed time for a stress wave to travel from one probe to another, the stress wave having been induced by the apparatus carried by the head,
marking the tree in response to the measure reliant upon a marking apparatus carried by the harvester head, and
harvesting then or later the tree.

16. The method of assessing trees using a harvester head of claim 1, said method comprising
positioning the harvester head with respect to the tree,
causing or allowing a harvester head carried apparatus to sense a sound or stress wave travelling from or past one probe to another in the tree, each probe being carried by the harvester head, and
assessing at least part of the tree as to a characteristic reliant directly or indirectly on the elapsed time of travel between the probes.

17. The method of claim 16 wherein the stress wave is created or induced by the harvester head or a device attached to the harvester head.

18. The method of claim 16 which further involves supplying the elapsed time or derivative thereof to the operator or an optimiser such that log making or product decisions relating to recovery of improved value can be made, accounting for velocity and the characteristic.

19. The method of claim 16 wherein there is one transmitting probe and two equidistant receiving probes and the shorter time or times of that one receiving probe is preferred to the other's.

20. A processor head or harvester head able to grapple a trunk of a standing or felled tree, to transversely cut a trunk and, when not cutting transversely, of driving itself along a grappled trunk, the processor head or harvester head comprising
first and second probes, each deployable to penetrate at least the bark of the trunk that is grappled and is being held stationary relative to the head, and each capable of being withdrawn from the deployed condition,
and wherein, whether through a probe or otherwise, a stress or sound wave generator of the head causes a stress or sound wave to travel longitudinally of the trunk at least from or past a first probe to a second probe spaced longitudinally of the trunk, and a processor determines an elapsed time of flight of the wave between the probes.

21. The head of claim 20 wherein the processor relates the time of flight, or a derivative thereof to a threshold.

22. The head of claim 20 wherein the first probe is a transmitter of the stress or sound wave and the second probe is a receiver of the stress or sound wave.

23. The head of claim 22 wherein the transmission and receiving surfaces of the probes face towards each other at an acute angle to the longitudinal axis of the trunk or log.

24. The head of claim 23 wherein the acute angle is about 45°.

25. The head of claim 23 wherein the probes are configured so as to reduce skewing upon deployment despite the acute angling.

26. The head of claim 20 wherein the first probe is a transmitter by virtue of a switch actuated hammer or other impactor acting thereon.

27. The head of claim 26 wherein the switch provides a transmission via cable or wireless means to the second probe or the processor so that the stress or sound wave is known to be coming having been initiated at a time related to switch actuation.

28. A method of harvesting, said method comprising
grappling a trunk of a standing tree with a harvester head,
deploying two probes from the head into the tree at positions spaced longitudinally of the trunk,
causing a stress or sound wave to travel longitudinally in the trunk from or past the first probe to be received by the second probe,
using processing means associated with inputs from at least one sensor or receiver, or both, associated with the second probe and at least one or more of a transmitter, sensor or switch associated with the first probe to obtain a time of flight of the stress or sound wave between the probes, and
using the output of the processing means to cause automatically or with operator intervention at least one of
(i) the head to fell the tree,
(ii) the head to mark the tree,
(iii) the head to fell the tree and to migrate on the felled tree to a distance from the felling cut and there to make a second cut, and
(iv) the head to fell the tree and to migrate on the felled tree to a distance from the felling cut and there to make a second cut and to mark or have marked the resultant log.

29. The method of claim 28 wherein, when the output is desirably to be structural timber or veneer, at least one or more of (i), (iii) and (iv):
(a) follows or involves an operator or head determined relativity of the tree or trunk to a minimum stem/log cross sectional or diameter threshold for structural timber and
(b) follows or involves, reliant on the output of the processing means, an operator or processing means determination that the time of flight or some value derived therefrom is suitable for milling as structural timber.

30. A processor head or harvester head able to grapple a trunk of felled tree or a log, said processor head or harvester head comprising
first and second probes, each deployable to penetrate at least the bark of a trunk or log that is grappled and is being held stationary relative to the head, and each capable of being withdrawn from the deployed condition,
and, whether through a probe or otherwise, a stress or sound wave generator of the head causes a stress or sound wave to travel longitudinally of the trunk or log at least from or past the first probe to the second probe spaced longitudinally of the trunk, and a processor determines an elapsed time of flight of the wave between the probes.

31. The head of claim 30 wherein the processor relates the time of flight, or a derivative thereof to a threshold.

32. The head of claim 30 wherein the first probe is a transmitter of the stress or sound wave and the second probe is a receiver of the stress or sound wave.

33. The head of claim 32 wherein the transmission and receiving surfaces of the probes face towards each other at an acute angle to the longitudinal axis of the trunk or log.

34. The head of claim 33 wherein the acute angle is about 45°.

35. The head of claim 33 wherein the probes are configured so as to reduce skewing upon deployment despite the acute angling.

36. The head of claim 30 wherein the first probe is a transmitter by virtue of a switch actuated hammer or other impactor acting thereon or therein.

37. The head of claim 36 wherein the switch provides a transmission via cable or wireless means to the second probe or via cable or wireless means to the processor so that the stress or sound wave is known to be coming having been initiated at a time related to switch actuation.

38. A method of processing, said method comprising
grappling a trunk of a felled tree or a log with a harvester or processor head,
deploying two probes from the head into the trunk or log at positions spaced longitudinally of the trunk or log,
causing a stress or sound wave to travel longitudinally in the trunk or log from or past the first probe to be received by the second probe,
using processing means associated with inputs from at least one sensor or receiver, or both, associated with the second probe and at least one or more of a transmitter, sensor or switch associated with the first probe to obtain a time of flight of the stress or sound wave between the probes, and
using the output of the processing means to cause automatically or with operator intervention at least one of
(a) the head to mark the trunk or log,
(b) the head to migrate relative to but on the trunk or log to a distance from the felling cut or a fresh cut and there to make a second cut,
(c) the head to migrate relative to but on the trunk or log to a distance from the felling cut or a fresh cut and there to make a second cut and to mark or have marked the resultant log,
(d) the head to migrate relative to but on the trunk or log to a distance from the felling cut or a fresh cut and there to make a second cut and to debranch or have debranched the resultant log,
(e) the head to migrate relative to but on the trunk or log to a distance from the felling cut or a fresh cut and there to make a second cut and to mark or have marked the resultant log and to debranch or have debranched the resultant log.

39. The method of claim 38 wherein, when the output is desirably to be structural timber or veneer, at least one or more of (a), (b), (c), (d) and (e):
(a) follows or involves an operator or head determined relativity of the trunk or log to a minimum stem or log cross sectional or diameter threshold for structural timber and
(b) follows or involves, reliant on the output of the processing means, an operator or processing means determination that the time of flight or some value derived therefrom is suitable for milling as structural timber.

40. A harvesting machine, the harvester head of a harvesting machine, or a harvesting head suitable for incorporation in a harvesting machine, comprising
the harvesting head directly or indirectly carries first and second longitudinally spaced probes adapted, when engaged with a tree or tree stem or logs thereof, to sense a stress wave travelling longitudinally in the tree, tree stem or log, the apparatus including means
(i) to initiate the longitudinal stress wave travel so that it will travel from one, or past the first probe, to, or past the second probe,
(ii) to determine an elapsed time of travel between the probes, and/or
(iii) to generate a decision signal for the fate of the tree/stem/log to the harvester operator and/or some responsive tree/stem/log marking or log making device.

* * * * *